United States Patent
D'Amore et al.

(10) Patent No.: US 7,102,021 B2
(45) Date of Patent: Sep. 5, 2006

(54) PROCESS FOR THE SELECTIVE OXIDATION OF ORGANIC COMPOUNDS

(75) Inventors: Michael Brian D'Amore, Wilmington, DE (US); Stephan Schwarz, Wilmington, DE (US)

(73) Assignee: Invista North America S.AR.L., Wilmington, DE (US)

( * ) Notice: Subject to any disclaimer, the term of this patent is extended or adjusted under 35 U.S.C. 154(b) by 844 days.

(21) Appl. No.: 09/836,920

(22) Filed: Apr. 18, 2001

(65) Prior Publication Data

US 2001/0025123 A1    Sep. 27, 2001

Related U.S. Application Data

(62) Division of application No. 09/270,332, filed on Mar. 16, 1999, now Pat. No. 6,251,851.

(60) Provisional application No. 60/084,523, filed on May 7, 1998.

(51) Int. Cl.
    C07D 301/19    (2006.01)
    C07D 301/06    (2006.01)

(52) U.S. Cl. ...................................... 549/529; 549/531

(58) Field of Classification Search ................ 549/529, 549/531
    See application file for complete search history.

(56) References Cited

U.S. PATENT DOCUMENTS 3,923,843 A    12/1975    Wulff

OTHER PUBLICATIONS

C.B. Knouw et al., Studies on the Catalytic Oxidation of Alkanes and Alkanes by Titanium Silicates, Journal of Catalysis, 149, 195-205 (1994).

*Primary Examiner*—Samuel Barts

(57) ABSTRACT

Disclosed is a process for oxidizing organic compounds using hydrogen peroxide to oxidize an oxidizable organic substrate in the presence of a silylated peroxide-activating metal/silica-containing catalyst and to a method of preparing such a catalyst.

5 Claims, No Drawings

PROCESS FOR THE SELECTIVE OXIDATION OF ORGANIC COMPOUNDS

This application is a divisional application of Ser. No. 09/270,332, filed on Mar. 16, 1999, now U.S. Pat. No. 6,251,851 which claims priority from provisional application 60/084,523, filed on May 7, 1998.

FIELD OF THE INVENTION

The invention generally relates to a process for oxidizing organic compounds. In particular, the invention relates to a process utilizing hydrogen peroxide to oxidize an oxidizable organic substrate in the presence of a silylated titania/silica-containing catalyst and to a preparation of this catalyst.

BACKGROUND OF THE INVENTION

Catalytic oxidation processes are important routes to many commercial chemicals. For example, numerous commercial processes for the epoxidation of olefins have been disclosed in the art. One such process involves the reaction of an organic hydroperoxide with an olefin in the presence of catalytic amounts of certain soluble transition metal compounds (e.g., molybdenum, tungsten, or vanadium napthenates). Some drawbacks to this process include co-production of an alcohol from the hydroperoxide, recovery of the soluble metal catalyst, and the sensitivity of the reaction to water.

Heterogeneous catalysts which overcome some of the aforesaid problems have also been developed. U.S. Pat. No. 3,923,843 claims a process for the epoxidation of an olefinically unsaturated compound comprising reacting the compound in the liquid phase with an organic hydroperoxide in the presence of a catalyst comprising an inorganic siliceous compound in chemical combination with an oxide or hydroxide of titanium. The catalyst is treated with an organic silylating agent before use. In the examples shown, the epoxide selectivity is increased from about 3% to about 15% when comparing the untreated catalyst to the silylated form.

Hydrogen peroxide is often employed as an oxidizing agent for the production of organic chemicals. A wide variety of organic compounds may be oxidized utilizing hydrogen peroxide, for example, olefins can be oxidized to epoxides (oxiranes) using this reagent.

Many titanosilicates have been reported to be useful as oxidation catalysts. For example, the catalytic oxidation of alkanes and alkenes by titanium silicates is disclosed in C. B. Khouw et al., "Studies on the Catalytic Oxidation of Alkanes and Alkenes by Titanium Silicates", Journal of Catalysis 149, 195–205 (1994). Such catalysts are used for the selective oxidation of n-octane using organic hydroperoxides as the oxidants at temperatures below 100° C. The absence of water is deemed critical for catalytic activity.

In this regard, there is a need for processes that can utilize aqueous hydrogen peroxide rather than organic hydroperoxides to provide both a safe and an efficient process for oxidizing organic compounds. The present invention satisfies that need, but yet can still be used with organic hydroperoxides, and also overcomes certain deficiencies inherent in the prior art. Other objects and advantages of the invention will become apparent to those skilled in the art upon reference to the detailed description which follows hereinafter.

SUMMARY OF THE INVENTION

The invention provides a process for oxidizing organic compounds comprising: contacting, in a zone of reaction, an oxidizable organic compound with a peroxide selected from the group consisting of hydrogen peroxide and organic hydroperoxides, in the presence of a catalytically effective amount of an insoluble catalyst comprising silicon oxide and an oxide of at least one peroxide-activating metal prepared by sol-gel techniques, wherein said catalyst is characterized by (i) the silicon to peroxide-activating atomic ratio is less than 10,000 to 1; (ii) is x-ray amorphous; (iii) possesses a Si—C infrared band; and (iv) has a surface area greater than 500 m²/g, a pore volume greater than 0.5 mL/g and an average pore diameter of greater than 4 nm.

Preferably, in the process of the invention, the organic compound is selected from the group consisting of:
(a) cyclic olefins and olefins according to the formula $R^1R^2C=CR^3R^4$,
wherein $R^1$, $R^2$, $R^3$ and $R^4$ are each independently —H; alkyl, wherein the alkyl group has from 1 to 16 carbon atoms; alkylaryl, wherein the alkylaryl group has from 7 to 16 carbon atoms; cycloalkyl, wherein the cycloalkyl group has from 6 to 10 carbon atoms; or alkylcycloalkyl, wherein the alkylcycloalkyl group has from 7 to 16 carbon atoms; and wherein said olefin can optionally containing halogen atoms (i.e., Cl, Br, F, and I);
(b) cyclic ketones according to the formula

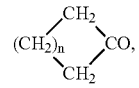

wherein n is an integer from 2 to 9;
(c) compounds of the formula $C_6H_5R^5$, wherein $R^5$ is —H, —OH; $C_1$ to $C_3$ straight chain, saturated or unsaturated hydrocarbon radicals, —CO₂H; —CN; —COC$_m$, wherein m is an integer from 1 to 6; —OC$_m$, wherein m is an integer from 1 to 6; or $NR^6R^7$, where $R^6$ and $R^7$ are each independently —H or $C_1$ to $C_3$ alkyl groups;
(d) alicyclic hydrocarbons according to the formula $R^8R^9CH_2$,
wherein $R^8$ and $R^9$ together from a link of (—CH₂—)$_p$, wherein p is an integer from 4 to 11;
(e) aliphatic hydrocarbons of the formula $C_qH_{2q+2}$, wherein q is an integer from 1 to 20; and
(f) alcohols according to the formula $R^{10}R^{11}CHOH$, wherein $R^{10}$ and $R^{11}$ are each independently —H; alkyl, wherein the alkyl group has from 1 to 16 carbon atoms; alkylaryl, wherein the alkylaryl group has from 7 to 16 carbon atoms; cycloalkyl, wherein the cycloalkyl group has from 6 to 10 carbon atoms; cycloalkyl wherein $R^{10}$ and $R^{11}$ taken together form a link containing 4 to 11 —CH₂— groups; or alkylcycloalkyl, wherein the alkylcycloalkyl group has from 7 to 16 carbon atoms.

The invention also provides a process for the preparation of an aerogel catalyst comprising synthesizing a catalyst comprising oxides of silicon and a peroxide-activating metal by (i) preparing a sol-gel containing silicon and a peroxide-activating metal; (ii) extracting the gel with a solvent to remove substantially all of the water from the gel and optionally removing the solvent; (iii) washing the gel with a solvent for the silylating agent; (iv) treating the gel with a silylation agent; (v) drying the treated gel at a temperature of from about ambient to about 130° C.; and optionally (vi) calcining the gel at a temperature of less than about 400° C.

The present invention further provides a catalyst composition comprising silica and an oxide of at least one peroxide-activating metal characterized by (i) having a silicon to peroxide-activating atomic ratio of less than 10,000 to 1; (ii) being x-ray amorphous; (iii) possessing a Si—C infrared band; and (iv) having a surface area greater than 500 $m^2/g$, a pore volume greater than 0.5 mL/g and an average pore diameter of greater than 4 nm.

DETAILED DESCRIPTION OF THE PREFERRED EMBODIMENTS

Peroxide-activating metals include, for example, silver, cobalt, cerium, manganese, iron, copper, molybdenum, tungsten, vanadium, titanium, chromium and mixtures thereof. A presently preferred metal is tetrahedrally coordinated titanium. Amorphous titania/silica aerogels prepared according to the process of this invention where the weight ratio of $TiO_2$ to $SiO_2$ is between 0.0005:1 and 0.5:1 are the preferred catalyst in the above-named oxidation reactions.

In accordance with this invention, gels containing silica and an oxide of the peroxide-activating metal are prepared by combining a silicate selected from the group consisting of $Si(OR^{12})_4$ and $SiR^{14}(OR^{13})_3$, $Si(OR^{12})_4$ and $SiH(OR^{13})_3$, where $R^{12}$ is a $C_1$ to $C_4$ alkyl group, $R^{13}$ is a $C_1$ to $C_8$ alkyl group and $R^{14}$ is H, $C_6H_5$ or $R^{13}$, where $C_6H_5$ is a phenyl group, with alkoxides of the peroxide-activating metals, selected from the group consisting of $—(OR^{13})_n$ where n is the valence of the peroxide-activating metal.

A solution of a concentrated mineral acid such as HCl, $HNO_3$ or $H_2SO_4$; or an organic acid with a $pK_a$ equal to or less than 4, such as formic and trifluoroacetic acids; or a base selected from the group consisting of ammonia, and a water-soluble organic amine such as methylamine and ethylamine; optionally water; and an alcohol selected from the group consisting of $R^{13}OH$, where $R^{13}$ is as defined above, is prepared. The $C_1$ to $C_4$ alcohols are preferred. The acidic or basic alcohol solution as defined above is added to the mixed oxide solution such that the alcohol to water ratio is greater than 2 by volume. After stirring at room temperature for at least five minutes, additional alcohol from the group described above is added in an amount such that the total alcohol to water ratio is less than 100. The mixture is stirred for between about 0.1 and 350 hours at temperature of from about 0° C. to about 50° C. to produce a gel.

For the preferred titanium-containing gels, the titanium source compound can be selected from the group consisting of $Ti(OR^{12})_4$, where $R^{12}$ is as defined above; Tyzor® organic titanates such as the acetylacetonate chelate, the ammonium lactate chelate, the triethanolamine chelate and the 2-ethylhexyl ester of orthotitanic acid; organotitanium compounds containing cyclopentadienyl groups such as $(C_5H_5)TiCl_3$ and $(C_5H_5)_2TiCl_2$, where $C_5H_5$ is a cyclopentadienyl group.

The water is removed from the gel by extraction with a protic solvent (e.g., an alcohol) or an aprotic solvent (e.g., acetone or tetrahydrofuran). If the silylating agent is not soluble in the extraction solvent, then a solvent in which it is soluble in such as acetone, toluene or tetrahydrofuran, is used to further extract the gel to remove the original solvent. The extracted gel is then stirred in a solution of a solvent and silylating agent. One skilled in the art would know which solvent or combination of solvents to use. The molar ratio of silylating agent:(Si +peroxide-activating metal) is between from about 0.1:1 to about 2:1, preferably 1.5:1.

Suitable silylating agents include organosilanes, organosilylamines, and organosilazanes. Examples of suitable silanes include chlorotrimethylsilane $((CH_3)_3SiCl)$, dichlorodimethylsilane $((CH_3)_2SiCl_2)$, bromochlorodimethylsilane $((CH_3)_2SiBrCl)$, chlorotriethylsilane $((C_2H_5)_3SiCl)$ and chlorodimethylphenylsilane $((CH_3)_2Si(C_6H_5)Cl)$. Examples of suitable silazanes include 1,2-diethyldisilazane $(C_2H_5SiH_2NHSiH_2C_2H_5)$, 1,1,2,2-tetramethyldisilazane $((CH_3)_2SiHNHSiH(CH_3)_2)$, 1,1,1,2,2,2-hexamethyldisilazane $((CH_3)_3SiNHSi(CH_3)_3)$, 1,1,2,2-tetraethyldisilazane $(C_2H_5)_2SiHNHSiH(C_2H_5)_2$ and 1,2-diisopropyldisilazane $((CH_3)_2CHSiH_2NHSiH_2CH(CH_3)_2)$.

Preferred silylating agents include silazanes and N,O-bis (trimethylsilyl)-trifluoroacetamide $(CF_3C(OSi(CH_3)_3)=NSi(CH_3)_3)$. These two agents do not generate corrosive hydrogen halides when they are used unlike the organosilanes.

The gel is separated from the solvent, washed with the solvent and dried at a temperature of from between room temperature and 110° C.

The gel exhibits a band in the infrared absorption region at about 1050 $cm^{-1}$ to about 1300 $cm^{-1}$ indicating the presence of an Si—C group in the gel. The Si—C group is selected from the group consisting of $(CH_3)_3Si$, $(CH_3)_2SiCl$, $(C_2H_5)_3Si$, $(CH_3)_2Si(C_6H_5)$, $C_2H_5SiH_2$, $(CH_3)_2SiH$, $(C_2H_5)_2SiH$ and $(CH_3)_2CHSiH_2$.

The peroxides useful for this invention include hydrogen peroxide and hydrocarbon hydroperoxides. For the hydrocarbon compounds, preferred are secondary and tertiary hydroperoxides of up to fifteen carbon atoms, especially tertiary alkyl hydroperoxides such as tertiary bytyl hydroperoxide; and alkyl hydroperoxides wherein the hydroperoxy group is on a carbon atom attached directly to an aromatic ring, e.g., α-hydroperoxy-substituted aralkyl compounds such as α-methylbenzyl hydroperoxide and cumene hydroperoxide.

A wide variety of organic compounds can be oxidized by the process of this invention. Presently preferred organic compounds are listed above in the "Summary of the Invention".

Olefins useful in the process of this invention may be any organic compound having at least one ethylenically unsaturated functional group (i.e., a carbon-carbon double bond) and may be a cyclic, branched, or straight chain olefin. The olefin is reacted with hydrogen peroxide to produce an epoxide (oxirane). The olefin may contain aryl groups such as phenyl. Preferably, the olefin is an aliphatic compound containing from 2 to 20 carbon atoms. Multiple double bonds may be present in the olefin, e.g., dienes, trienes, and other polyunsaturated substrates. The double bond may be in a terminal or internal position of the olefin or may form part of a cyclic structure as in cyclohexene. Other, non-limiting examples of suitable organic compounds include unsaturated fatty acids or esters and oligomeric or polymeric unsaturated compounds such as polybutadiene.

The olefin may optionally contain functional groups such as halide, carboxylic acid, ether, hydroxy, thio, nitro, cyano, ketone, acyl, ester, amino, and anhydride.

Preferred olefins include ethylene, propylene, butenes, butadiene, pentenes, isoprene, and hexenes.

Mixtures of olefins may be epoxidized and the resulting mixtures of epoxides may be used in mixed form or separated into the component epoxides.

Olefins especially preferred for the process of this invention include those of the formula $R^1R^2C=CR^3R^4$, wherein $R^1$, $R^2$, $R^3$ and $R^4$ are each independently selected from the group consisting of H and $C_1$ to $C_{12}$ straight chain, saturated, or unsaturated hydrocarbon radicals.

Cyclic ketones useful in the process of this invention include cyclopentanone, cyclohexanone. The cyclic ketone is reacted with the in-situ generated hydrogen peroxide to produce lactones. For example, cyclopentanone is converted to valerolactone and cyclohexanone is converted to caprolactone. Also, in the presence of ammonia cyclohexanone is converted to cyclohexanone oxime.

Compounds of the formula $C_6H_5R^5$, wherein $R^5$ is selected from a group as defined in the "Summary of the Invention", are reacted with hydrogen peroxide to produce phenols. For example, phenol, itself, is converted to hydroquinone and toluene is converted to catechol.

Alicyclic hydrocarbons of the formula $R^8R^9CH_2$, wherein $R^8$ and $R^9$ together form a link selected from the group consisting of $(-CH_2-)_p$, wherein p is an integer from 4 to 11 useful in the process of this invention include cyclohexane and cyclododecane. Alicyclic hydrocarbons of the formula $R^8R^9CH_2$ are reacted with hydrogen peroxide to produce ketones and alcohols. For example, cyclohexane is converted to a mixture of cyclohexanol and cyclohexanone and cyclododecane is converted to a mixture of cyclododecanol and cyclododecanone.

Aliphatic hydrocarbons of the formula $C_qH_{2q+2}$, wherein q is an integer from 1 to 20 useful in the process of this invention include hexane and heptane. Aliphatic hydrocarbons of the formula $C_qH_{2q+2}$ are reacted with hydrogen peroxide to produce alcohols and ketones.

Alcohols according to the formula $R^{10}R^{11}CHOH$, wherein $R^{10}$ and $R^{11}$ are as defined above include 2-butanol, cyclohexanol, and cyclododecanol. These alcohols are oxidized to 2-butanone, cyclohexanone, and cyclododecanone, respectively.

In another embodiment of this invention, oximes can be prepared by reacting cyclic ketones of the formula

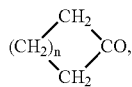

wherein n is an integer from 2 to 9, with hydrogen peroxide and ammonia in the liquid phase in the presence of the catalysts of this invention and then recovering the oxime product.

The reaction may also be conducted in organic solvents. Some preferred organic solvents are hydrocarbons such as hexane, benzene, methylene chloride, acetonitrile, lower aliphatic alcohols, ketones and dioxane, dimethylformamide and dimethylsulfoxide and mixtures thereof. Preferably, the solvents which are used are ones in which the substrate and products of the reaction are highly soluble.

The reaction is typically conducted at temperatures of from about 0° C. to about 200° C., preferably from about 25° C. to about 150° C. The reaction pressure is typically from about 1 atmosphere to about 100 atmospheres.

The oxidation products are recovered from the product mixtures by conventional techniques such as fractional distillation, extraction, and crystallization.

Without further elaboration, it is believed that one skilled in the art can, using the preceding description, utilize the present invention to its fullest extent. The following specific embodiments are, therefore, to be construed as merely illustrative, and are not to limit the remainder of the invention in any way whatsoever. All percentages are by weight unless otherwise indicated.

EXAMPLES

Example 1

Preparation of $SiO_2/TiO_2$ Catalyst with Hexamethyldisilazane (HMDS)

a. Preparation of Modified Titanium-isopropoxide (Ti-iprop) Solution

Ti-iprop (28.4 g) and isopropyl alcohol (IPA, 30 mL) are mixed in a drybox in a 200 mL round-bottom flask. Acetylacetone (acac, 10.01 g) in IPA (10 mL) are added. This solution is refluxed for 1 hour and cooled. The IPA was removed by vacuum and the remaining yellow paste was redissolved in IPA and made up to 100 mL in a volumetric flask. This is a 1M solution of Ti-acac.

b. Solgel Preparation

In the drybox, the Ti-acac solution (25 mL), tetramethylorthosilicate (45.66 mL) and IPA (44 mL) were mixed in a 500 mL plastic bottle. A solution of conc. HCl (2.4 mL), $H_2O$ (29.2 mL) and IPA (30 mL) were added. After stirring at room temperature for 5 minutes, additional IPA (168 mL) was added. This mixture was stirred for 90 hours. The Si:Ti atomic ratio of the gel as charged is 12:1.

c. Solgel Modification

The gel was extracted in a Soxhlet apparatus with IPA for 24 hours and twice with hexane for 24 hours. The extracted gel was stirred in a solution of hexane (500 mL) and hexamethyldisilazane (78.6 g) at room temperature for 90 hours. After filtering, the gel was washed twice with hexane (750 mL) at room temperature.

d. Drying/Calcination

The gel was then air dried at room temperature for 24 hours and then dried in a vacuum oven at 110° C. for 24 hours. The Si:Ti atomic ratio of the material was 15.6:1.

The catalyst of had an infrared band attributable to the $-Si-(CH_3)_3$ group at about 1260 $cm^{-1}$. This material was designated Cat. 1.

Another sample of Cat. 1 was calcined at 450° C. in air for 4 hours. The Si:Ti atomic ratio of the material was 21.5:1. This material was designated Cat. 1A.

Example 2

Preparation of $SiO_2/TiO_2$ Catalyst with Trimethylsilylchloride (TMSiCl)

Steps a to d of Example 2 were repeated except that in step c TMSiCl (52.96 g) was used. The final product had a Si:Ti ratio of 126:1, indicating significant loss of Ti during sylation of the gel. This material was designated Cat. 2.

Example 3

Preparation of $SiO_2/TiO_2$ Catalyst with Bis(trimethylsilyl)trifluoroacetamide (BSTFA)

Steps a to d of Example 2 were repeated except that in step c BSTFA (125.48 g) was used. The final product had a Si:Ti ratio of 15.7:1. This material was designated Cat. 3.

The catalysts prepared in Examples 2 and 3 had an infrared band at ~1260 $cm^{-1}$, indicating $-Si-(CH_3)_3$ groups.

Example 4

Epoxidation of 1-Octene

A mixture of 1-octene (4.13 g), 10% hydrogen peroxide (2.04 g), and Cat. 1 (209 mg) was stirred at room temperature for 23 hours. GC analysis of the organic product showed a 10% yield to 1,2-octane epoxide based on hydrogen peroxide.

Example 5

Epoxidation of Cis-Cyclooctene

A mixture of cis-cyclooctene (2.44 g), 10% hydrogen peroxide (1.13 g), and Cat. 1 (51 mg) was stirred at room temperature for 23 hours. GC analysis of the organic product showed a 28% yield to cyclooctane epoxide based on hydrogen peroxide.

Example 6

Epoxidation of 1-Octene

A mixture of 1-octene (2.06 g), 10% hydrogen peroxide (1.01 g), and Cat. 1A (50 mg) was stirred at room temperature for 50 hours. GC analysis of the organic product showed a 0.2% yield to 1,2-octane epoxide based on hydrogen peroxide.

Example 7

Epoxidation of 1-Octene

A mixture of 1-octene (2.14 g), 10% hydrogen peroxide (1.21 g), and Cat. 2 (50 mg) was stirred at room temperature for 24 hours. GC analysis of the organic product showed a 5% yield to 1,2-octane epoxide based on hydrogen peroxide.

Example 8

Epoxidation of Cis-Cyclooctene

A mixture of cis-cyclooctene (2.44 g), 10% hydrogen peroxide (1.13 g), and Cat. 2 (53 mg) was stirred at room temperature for 2 hours. GC analysis of the organic product showed a 19% yield to cyclooctane epoxide based on hydrogen peroxide.

Example 9

Epoxidation of 1-Octene

A mixture of 1-octene (2.13 g), 10% hydrogen peroxide (1.07 g), and Cat. 3 (56 mg) was stirred at room temperature for 24 hours. GC analysis of the organic product showed a 10% yield to 1,2-octane epoxide based on hydrogen peroxide.

Example 10

Epoxidation of Cis-Cyclooctene

A mixture of cis-cyclooctene (2.35 g), 10% hydrogen peroxide (1.15 g), and Cat. 3 (55 mg) was stirred at room temperature for 24 hours. GC analysis of the organic product showed a 35% yield to cyclooctane epoxide based on hydrogen peroxide.

The invention claimed is:

1. A process for oxidizing organic compounds comprising:
contacting, in a zone of reaction, an oxidizable organic compound with a peroxide selected from the group consisting of hydrogen peroxide and organic hydroperoxides, in the presence of a catalytically effective amount of an insoluble catalyst comprising silicon oxide and an oxide of at least one peroxide-activating metal prepared by sol-gel techniques, wherein said catalyst is characterized by (i) the silicon to peroxide-activating atomic ratio is less than 10,000 to 1; (ii) is x-ray amorphous; (iii) possesses a Si—C infrared band; and (iv) has a surface area greater than 500 m$^2$/g, a pore volume greater than 0.5 mL/g and an average pore diameter of greater than 4 nm.

2. The process of claim 1 wherein the organic compound is selected from the group consisting of:
   (a) cyclic olefins and olefins according to the formula $R^1R^2C=CR^3R^4$,
   wherein $R^1$, $R^2$, $R^3$ and $R^4$ are each independently —H; alkyl, wherein the alkyl group has from 1 to 16 carbon atoms; alkylaryl, wherein the alkylaryl group has from 7 to 16 carbon atoms; cycloalkyl, wherein the cycloalkyl group has from 6 to 10 carbon atoms; or alkylcycloalkyl, wherein the alkylcycloalkyl group has from 7 to 16 carbon atoms; and wherein said olefin can optionally containing halogen atoms;
   (b) cyclic ketones according to the formula

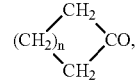

wherein n is an integer from 2 to 9;
   (c) compounds of the formula $C_6H_5R^5$, wherein $R^5$ is —H, —OH; $C_1$ to $C_3$ straight chain, saturated or unsaturated hydrocarbon radicals, —CO$_2$H; —CN; —COC$_m$, wherein m is an integer from 1 to 6; —OC$_m$, wherein m is an integer from 1 to 6; or NR$^6$R$^7$, where $R^6$ and $R^7$ are each independently —H or $C_1$ to $C_3$ alkyl groups;
   (d) alicyclic hydrocarbons according to the formula $R^8R^9CH_2$,
   wherein $R^8$ and $R^9$ together from a link of (—CH$_2$—)$_p$, wherein p is an integer from 4 to 11;
   (e) aliphatic hydrocarbons of the formula $C_qH_{2q+2}$, wherein q is an integer from 1 to 20; and
   (f) alcohols according to the formula $R^{10}R^{11}CHOH$, wherein $R^{10}$ and $R^{11}$ are each independently —H; alkyl, wherein the alkyl group has from 1 to 16 carbon atoms; alkylaryl, wherein the alkylaryl group has from 7 to 16 carbon atoms; cycloalkyl, wherein the cycloalkyl group has from 6 to 10 carbon atoms; cycloalkyl wherein $R^{10}$ and $R^{11}$ taken together form a link containing 4 to 11 —CH$_2$— groups; or alkylcycloalkyl, wherein the alkylcycloalkyl group has from 7 to 16 carbon atoms.

3. The process of claim 1 wherein the peroxide-activating metal is selected from the group consisting of silver, cobalt, cerium, manganese, iron, copper, molybdenum, tungsten, vanadium, titanium, chromium and mixtures thereof.

4. The process of claim 3 wherein the peroxide-activating metal is tetrahedrally coordinated titanium.

5. The process of claim 1 wherein the catalyst is an amorphous titania/silica aerogel wherein the weight ratio of TiO$_2$ to SiO$_2$ is between 0.0005:1 and 0.5:1.

* * * * *